United States Patent
Zhang et al.

(10) Patent No.: US 10,646,496 B2
(45) Date of Patent: May 12, 2020

(54) JOINT APPLICATION OF STATIN AND ADRENOCORTICAL HORMONE FOR TREATING CHRONIC SUBDURAL HEMATOMA

(71) Applicants: Jianning Zhang, Tianjin (CN); Rongcai Jiang, Tianjin (CN); Dong Wang, Tianjin (CN)

(72) Inventors: Jianning Zhang, Tianjin (CN); Rongcai Jiang, Tianjin (CN); Dong Wang, Tianjin (CN); Wei Quan, Tianjin (CN)

(73) Assignees: Jianning Zhang, Tianjin (CN); Rongcai Jiang, Tianjin (CN); Dong Wang, Tianjin (CN)

( * ) Notice: Subject to any disclaimer, the term of this patent is extended or adjusted under 35 U.S.C. 154(b) by 0 days.

(21) Appl. No.: 15/579,897

(22) PCT Filed: Dec. 29, 2016

(86) PCT No.: PCT/CN2016/000720
§ 371 (c)(1),
(2) Date: Dec. 5, 2017

(87) PCT Pub. No.: WO2017/124213
PCT Pub. Date: Jul. 27, 2017

(65) Prior Publication Data
US 2018/0177802 A1    Jun. 28, 2018

(30) Foreign Application Priority Data

Jan. 20, 2016  (CN) .......................... 2016 1 0035891

(51) Int. Cl.
| | | |
|---|---|---|
| A61K 31/573 | (2006.01) | |
| A61K 31/402 | (2006.01) | |
| A61K 31/40 | (2006.01) | |
| A61K 31/366 | (2006.01) | |
| A61K 31/505 | (2006.01) | |
| A61P 25/00 | (2006.01) | |

(52) U.S. Cl.
CPC .......... *A61K 31/573* (2013.01); *A61K 31/366* (2013.01); *A61K 31/40* (2013.01); *A61K 31/505* (2013.01); *A61P 25/00* (2018.01)

(58) Field of Classification Search
CPC ........................... A61K 31/573; A61K 31/402
USPC ................................ 514/171, 408
See application file for complete search history.

(56) References Cited

PUBLICATIONS

Jameel, Ashmal et al, International Journal of Inflammation (2013), vol. 31(12), pp. 201-203. (Year: 2013).*

(Continued)

*Primary Examiner* — Craig D Ricci
*Assistant Examiner* — Janet L. Coppins
(74) *Attorney, Agent, or Firm* — PROI Intellectual Property US

(57) ABSTRACT

The present invention provides joint use of stain and adrenocortical hormone for preparing a pharmaceutical product for the treatment of chronic subdural hematoma. The pharmaceutical product according to the present invention is capable of accelerating hematoma absorption and improving a therapeutic effect of single oral administration of a statin-based pharmaceutical product, and the dose of the adrenocortical hormone-based pharmaceutical product used is ¹⁄₁₀ of the dose used in a large-dose hormonal therapy.

2 Claims, 8 Drawing Sheets

(56) References Cited

PUBLICATIONS

Delgado-Lopez et al, Neurocirugia (2009), vol. 20(4), pp. 346-359. (Year: 2009).*
Li et al, J. Neurological Sciences (2014), vol. 341, pp. 88-96. (Year: 2014).*
Li et al, J Neurological Sciences, vol. 341 (2014), pp. 88-96. (Year: 2014).*

* cited by examiner

JOINT APPLICATION OF STATIN AND ADRENOCORTICAL HORMONE FOR TREATING CHRONIC SUBDURAL HEMATOMA

CROSS REFERENCE TO RELATED APPLICATIONS

The present application is the US national stage of International Patent Application PCT/CN2016/000720 filed on Dec. 29, 2016, which, in turn, claims priority to Chinese Patent Application CN 201610035891.3 filed on Jan. 20, 2016.

TECHNICAL FIELD

The present invention pertains to the technical field of pharmaceutical supplies containing effective ingredients, and in particular, relates to joint use of statin and dexamethasone and a structural analogue thereof for the treatment of chronic subdural hematoma.

BACKGROUND

People having been exploring and studying the chronic subdural hematoma (CSDH) for more than a century, and the earliest study may be dated back to more than 150 years ago. It is documented that Virchow first studied the formation mechanism of the chronic subdural hematoma, and Virchow firstly depicted this disease and proposed the hypothesis that the inner dura matter inflammatory hemorrhage is the cause to the CSDH, that is, Pachymeningitis Theory. Afterwards, pathological examinations and electron microscopy and other series of studies have found that the chronic subdural hematoma capsule contains a large number of abnormal sinusoid lacunar. Since then, the subdural hematoma "newborn envelop repeated bleeding theory" is gradually concentrated by the academic attention.

In recent years, fundamental studies on the chronic subdural hematoma have identified that the disease is an inflammatory angiogenic disease, and thus view point has been increasingly accepted by the public. The levels of inflammatory cytokines IL-6, IL-8 and IL-10 in the hematoma fluid are significantly increased relative to the peripheral blood, the levels IL-6 and VEGF in the hematoma fluid of the recurrence patients are significantly increased relative to the non-recurrence patients, and the VEGF expression in the adventitia of the hematoma cavity is significantly increased. The levels of these cytokines are closely related to the recurrence of hematoma. At the same time, the researchers have also found that angiogenesis-related factors PlGF, VEGF, bFGF, MMP-2 and MMP-9 in the hematoma fluid are significantly increased, and Ang-1 and Ang-2mRNA promoting generation of vessels in the adventitia of the hematoma are increased. A decrease of the proportion thereof indicates an increase of generation of new vessels. The combination of the inflammatory factors and the angiogenic factors may be a key factor in the formation of CSDH.

It is well recognized that surgical treatment of the chronic subdural hematoma is the most effective treatment, especially in the treatment of the patients with large amounts of hematoma, obvious clinical symptoms and a midline shift greater than 5 mm. Through the surgical operation, intracranial hypertension and hernia may be quickly relieved. In addition to the surgical treatment, other conservative treatments of the chronic subdural hematoma mainly include: pure resting lying guard, intracranial pressure reduction by mannitol dehydration, anti-epileptic treatment, glucocorticoid therapy, angiotensin-converting enzyme inhibitor, and even radiation therapy.

In recent years, a large number of reports reveal studies on the treatment of chronic subdural hematoma using hormones. For example, in the year of 2005, Sun reported that 25 patients who were intolerant to the surgical operation and have complications were treated using dexamethasone for 21 days (4 mg/6 h), and finally 23 patients (84%) had a better prognosis. In addition, the recurrences are significantly reduced for the patients after they were continuous administered with dexamethasone (DXM) for 2 weeks upon the surgical operation. Likewise, a separate retrospective study by Dran and Berghause has demonstrated that the death risk of the group postoperatively administered with dexamethasone is reduced by 3 folds as compared with the group with no administration of dexamethasone, and perioperative administration of dexamethasone may reduce the postoperative recurrence. A perspective study using dexamethasone by Delgado-Lopez et al. has also proved that it is effective to treat the chronic subdural hematoma with hormone. In the year of 2014, a randomized double-blind controlled clinical trail (DRESH trail) carried out by a China-Austria multicenter planed to admit 820 patients, and the finally result of the study would further clarify whether perioperative administration of dexamethasone can reduce postoperative CSDH recurrence. A placebo-controlled trail has been carried out in an experimental group and a control group in Canada each involving 10 patients (registration number: NCT02362321), and the final result shows that 1 patient in the group of dexamethasone is transferred to the surgical treatment whereas 3 patients in the group of placebo are transferred to the surgical treatment. However, in the above trails, a large mount of hormones is used. The excessive use of dexamethasone may cause obesity, gastrointestinal damage and other steroid-related complications. Therefore, the hormone-related therapy has not been promoted, and most applications thereof are limited to surgery auxiliary medication.

Chinese Patent application No. 201210014181.4, entitled with "USE OF STATIN IN PREPARING DRUG FOR THE TREATMENT OF CHRONIC SUBDURAL HEMATOMA" has disclosed that the statin may obviously promote absorption of chronic hematoma, such that hematoma of some patients is absorbed through conservative treatment with drugs, thereby avoiding surgical treatment. However, this therapy takes long to come into effect, and it is almost sixth months, or at least one month, from the time the patients receive the treatment and the time the hematoma is absorbed, which gives confusion to some patients.

SUMMARY

The present invention is intended to solve the problems that treatment for chronic subdural hematoma using statin takes long and use of a large amount of hormones causes complications to patients, and address the technical prejudice hold by a person skilled in the art against use of hormones.

The present invention provides joint use of statin and adrenocortical hormone for the treatment of chronic subdural hematoma, and in particular, provides use of statin and adrenocortical hormone for preparing a pharmaceutical product for the treatment of chronic subdural hematoma.

Preferably, the statin is one or a combination of atorvastatin, simvastatin and rosuvastatin.

Preferably, the adrenocortical hormone is one or a combination of dexamethasone, prednisone, methylprednisolone and hydrocortisone.

More preferably, the adrenocortical hormone is dexamethasone or prednisone.

Preferably, a mass ratio of the statin to the adrenocortical hormone in an equivalent dose is 40:3.

More preferably, the statin is atorvastatin, and the adrenocortical hormone is dexamethasone, wherein a mass ratio of the atorvastatin to the dexamethasone is 40:3.

Administration doses of the statin and the adrenocortical hormone are as follows:

30 mg/day, 2.25 mg/day; or 20 mg/day, 1.5 mg/day; or 10 mg/day, 0.75 mg/day; wherein the doses are administered 1 time per day or 2 to 3 times per day.

Preferably, administration doses of the statin and the adrenocortical hormone are as follows:
administration in the first week: 30 mg/day, 2.25 mg/day; administration for second to third weeks: 20 mg/day, 1.5 mg/day; or
administration in the fourth week: 10 mg/day, 0.75 mg/day.

The present invention further provides a pharmaceutical composition, comprising: a first active ingredient in a therapeutically effective amount, the first active ingredient being statin; and a second active ingredient in a therapeutically effective amount, the second active ingredient being adrenocortical hormone, and preferably, dexamethasone and a structural analogue thereof.

Preferably, the statin is one or a combination of atorvastatin, simvastatin and rosuvastatin.

Preferably, the structural analogue of the dexamethasone is dexamethasone or prednisone.

Preferably, a mass ratio of the first active ingredient to the second active ingredient in an equivalent dose is 40:3.

The equivalent dose in the present invention refers to a relative drug concentration or dose in which an equivalent effect may be caused, and reflects a relationship between the drug effect and the drug dose. In the present invention, the mass ratio 40:3 of the first active ingredient to the second active ingredient in the equivalent dose is determined based on the administration doses of the atorvastatin and the dexamethasone. That is, the mass ratio of the atorvastatin to the dexamethasone is 40:3. Other statins all need to be used in a dose that is effect-equivalent to the atorvastatin, and other structural analogues of the dexamethasone all need to be used in a dose that is effect-equivalent to the dexamethasone.

In clinical use, a conversion scale of the statins in an equivalent dose is rosuvastatin: atorvastatin: simvastatin=1: 3:4 (a maximum dose of the simvastatin is 40 mg/day).

A conversion scale of the structural analogues of the dexamethasone in an equivalent dose is dexamethasone: prednisone=1:5.

Therefore, in the pharmaceutical composition, a mass ratio of the rosuvastatin to the dexamethasone is 40:9.

In the pharmaceutical composition, a mass ratio of the rosuvastatin to the prednisone is 8:9.

In the pharmaceutical composition, a mass ratio of the atorvastatin to the prednisone is 8:3.

Therefore, in the pharmaceutical composition, a mass ratio of the simvastatin to the dexamethasone is 160:9.

In the pharmaceutical composition, a mass ratio of the simvastatin to the prednisone is 32:9.

In the pharmaceutical composition, administration doses of the statin and the adrenocortical hormone are as follows: 30 mg/day, 2.25 mg/day; or 20 mg/day, 1.5 mg/day; or 10 mg/day, 0.75 mg/day;
wherein the doses are administered 1 time per day or 2 to 3 times per day.

Preferably, oral administration doses of the atorvastatin and the dexamethasone in the pharmaceutical composition are as follows:
administration in the first week: 30 mg/day, 2.25 mg/day; administration in the second to third weeks: 20 mg/day, 1.5 mg/day; or
administration in the fourth week: 10 mg/day, 0.75 mg/day.

The present invention further provides use of the pharmaceutical composition for preparing a pharmaceutical product for the treatment of chronic subdural hematoma.

The present invention achieves the following beneficial effects:

(1) Compared with the use of the stain alone, the combination of the drugs according to the present invention significantly accelerates absorption of hematoma, an average time duration when the hematoma was significantly reduced was about 2 weeks, and an average time duration when the hematoma disappeared was about 1.5 months. This greatly improved the therapeutic effect achieved by oral administration of the statin alone. Even when the statin treatment was not effective, adding hormones could achieve satisfactory therapeutic effects without any other adverse effects.

(2) The amount of hormones used in the present invention is 1/10 of that of the large dose of hormones (16 to 24 mg/d), which greatly reduces the incidence of related complications (gastrointestinal bleeding, ulcer, and infection). In addition, a person skilled in the art would readily think that the greater the dose of hormones, the more obvious the therapeutic effect. However, the present invention combines the statin with a small dose of dexamethasone, overcomes the technical prejudice, and achieves an unexpected therapeutic effect. Further, the treatment cycle is significantly shortened, and thus pains caused by the surgery to the patients are avoided.

(3) The pharmaceutical composition according to the present invention has a good therapeutic effect and has an broad application prospect and clinical significance.

DETAILED DESCRIPTION

For further interpretation of the technical solutions of the present invention and the technical effects to be achieved thereby, hereinafter the present invention is further described with reference to the accompanying drawings and the exemplary embodiments.

1. A Small Dose of Atorvastatin Promotes Absorption of Subdural Hematoma.

Figure 1:
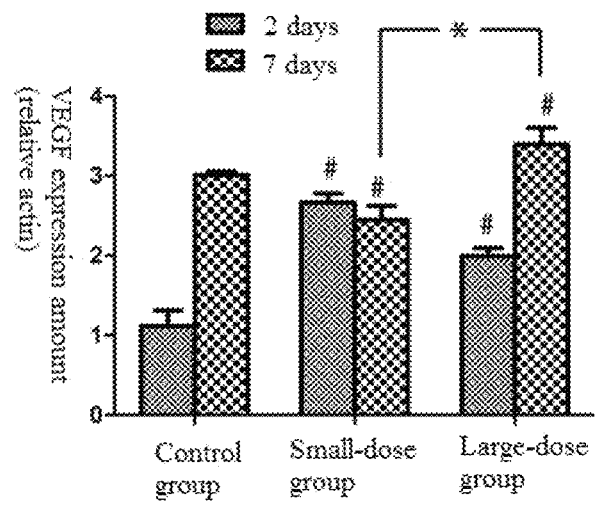
FIG. 1 is an influence diagram of different doses of atorvastatin to a VEGF factor expression amount in a hematoma capsule of a rat according to the present invention.
Figure 2:
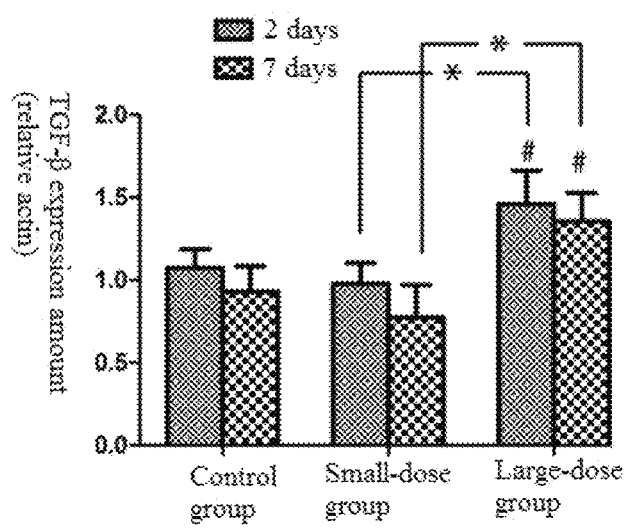
FIG. 2 is an influence diagram of different doses of atorvastatin to a TGF-β factor expression amount in a hematoma capsule of a rat according to the present invention.
Figure 3:
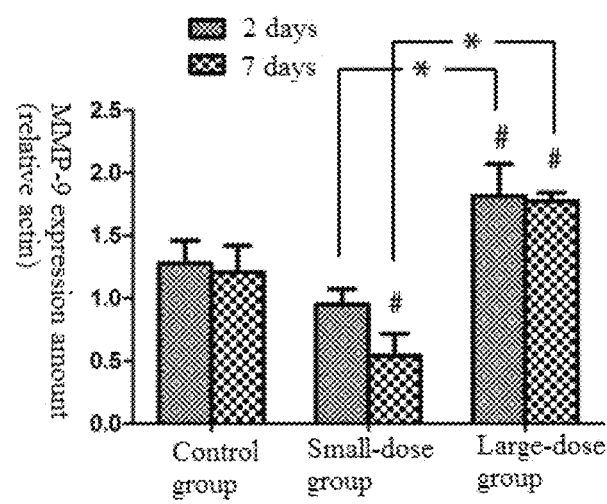
FIG. 3 is an influence diagram of different doses of atorvastatin to an MMP-9 factor expression amount in a hematoma capsule of a rat according to the present invention.
Figure 4:
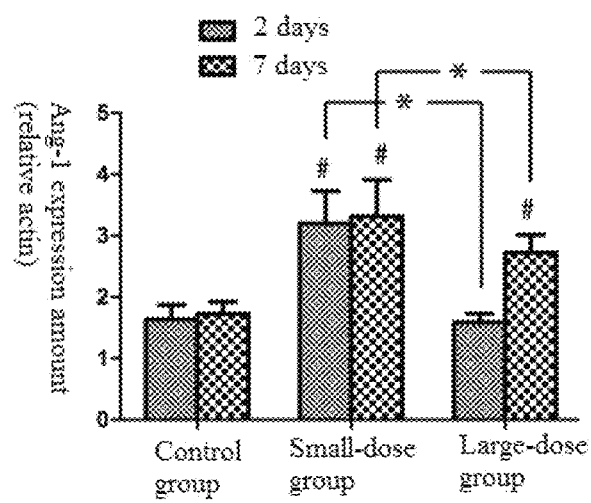
FIG. 4 is an influence diagram of different doses of atorvastatin to an Ang-1 factor expression amount in a hematoma capsule of a rat according to the present invention.
Figure 5:
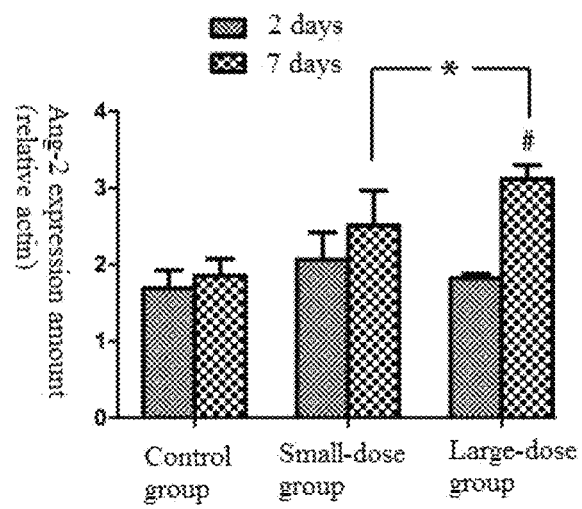
FIG. 5 is an influence diagram of different doses of atorvastatin to an Ang-2 factor expression amount in a hematoma capsule of a rat according to the present invention.
Figure 6:
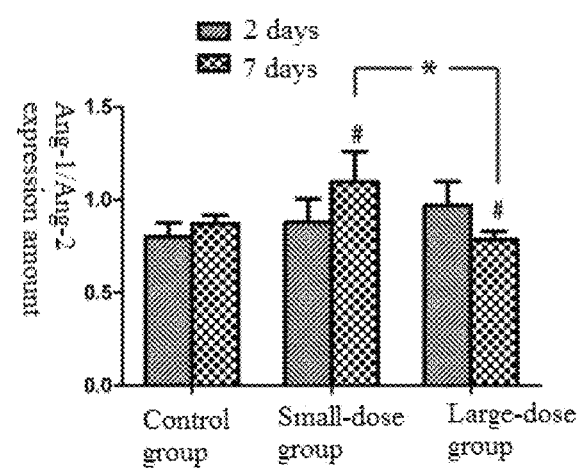
FIG. 6 is a variation diagram of ratios of atorvastatin to an Ang-1/Ang-2 factor in a hematoma capsule of a rat according to the present invention.
Figure 7:
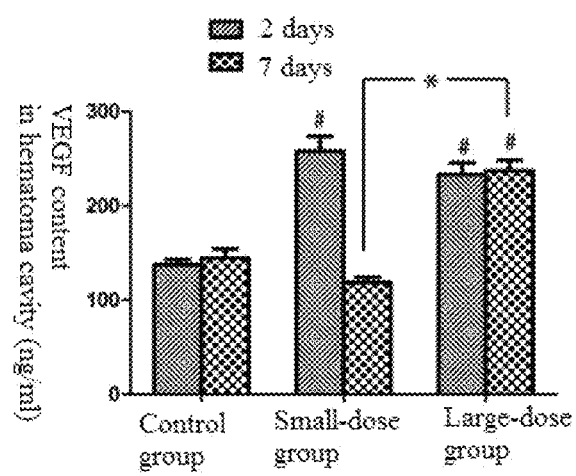
FIG. 7 is an influence diagram of different doses of atorvastatin to a VEGF factor expression amount in a hematoma cavity of a rat according to the present invention.
Figure 8:
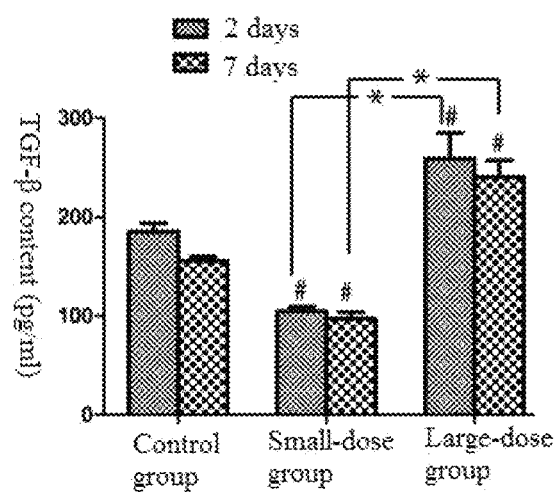
FIG. 8 is an influence diagram of different doses of atorvastatin to a TGFβ factor expression amount in a hematoma cavity of a rat according to the present invention.
Figure 9:
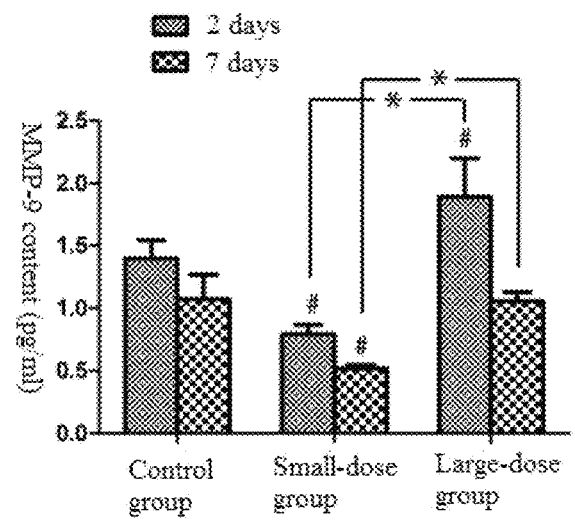
FIG. 9 is an influence diagram of different doses of atorvastatin to an MMP-9 factor expression amount in a hematoma cavity of a rat according to the present invention.

Experimental animals were divided into three groups: a control group, a small-dose group (3 mg/kg/day, equivalent to 80-20 mg/day for adults), and a large-dose group (8 mg/kg/day, equivalent to 80-100 mg/day for adults) by improving subdural modeling of rats based on varied oral administration doses of the atorvastatin. Dynamic changes of the hematoma volume of the rats by using MRI, HE straining, transmission electron microscopy, immunohistochemistry, flow cytometry, real-time quantitative PCR and ELISA techniques were used to measure the morphological features of neovascular hemorrhagic conjunctivitis at different observation points, the number of endothelial progenitor cells, neovascularization and smooth muscle cell density, expression of VEGF, TGF-β, MMP-9 and Ang-1/2 in peripheral blood and hematoma envelope after the modeling. The experiment results showed that at the time of 2 days, mRNA expression of hematoma capsule VEGF (FIG. 1 and FIGS. 7) and Ang1 was significantly higher in the small-dose group (FIG. 4), whereas the large-dose group showed significantly higher expressions of VEGF, TGFβ and MMP-9 (FIG. 1 to FIG. 4, and FIG. 7 to FIG. 9). At the time of 7 days after the operation, the expression levels of VEFG and MMP-9 in the small-dose group were significantly lower, and the ratio of Ang1 to Ang-1/Ang-2 (FIG. 4 to FIG. 6) was significantly higher than those in the control group and the large-dose group. However, the large-dose group showed high expressions of the VEGF, TGF-β, MMP-9 and Ang2.

In FIG. 1 to FIG. 9, "#" denotes a statistically significant difference in the small-dose group and the large-dose group as compared with the control group; and "*" denotes a statistically significant difference between the small-dose group and the large-dose group.

Through the experiments, it was concluded that the absorption rate of subdural hemotama was not only related to the number of neovascularization of hematoma capsule, but also related to the mature and stable blood vessel formation in the capsule. The small-dose atorvastatin would inhibit the local inflammatory reaction in the hematoma cavity, promote formation of mature and stable blood vessels, such that absorption of hematoma was accelerated.

2. Atorvastatin in Combination with a Small Dose of Dexamethasone Promotes Absorption of Subcutaneous Hematoma of a Rat.

Figure 10:
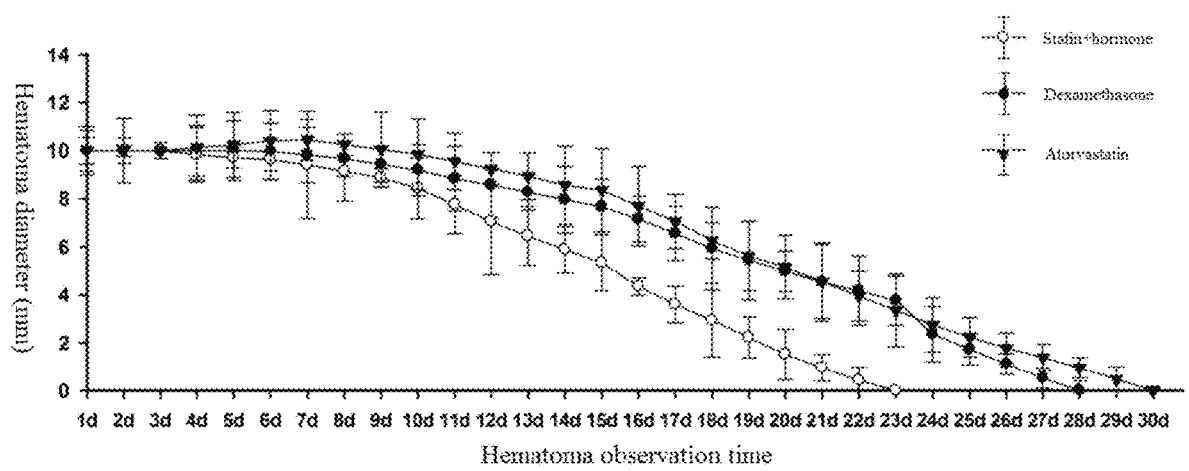
FIG. 10 is an influence diagram of different treatment groups to subcutaneous hematoma volume of a rat according to the present invention.

Through the mouse subcutaneous injection model, by using a small dose of atorvastatin and a large dose of dexamethasone, and a small dose of atorvastatin in combination with a small dose of dexamethasone, hematoma changes were dynamically observed. The experiment results showed (see Table 1) that use of the small dose of atorvastatin in combination with the small dose of dexamethasone significantly accelerated absorption of hematoma (FIG. 10); as compared with the group of the small-dose of atorvastatin, the hematoma absorption speed in the group of the large-dose of atorvastatin was not significantly improved, whereas the hormone-caused complications are significantly increased and the death rate was significantly improved. The small dose of atorvastatin in combination with the small dose of dexamethasone exerted a significant synergistic effect, and the specific molecular biological level still need further study.

TABLE 1

Dynamic changes of hematoma of rats in different treatment groups

| Item/Group | Number of rats | Rats died in the treatment | Injury infection | Poor condition |
|---|---|---|---|---|
| Small-dose atorvastatin 3 mg/kg/day | 30 | 2 | 1 | 3 |
| Large-dose atorvastatin 5 mg/kg/day | 28 | 7 | 4 | 6 |
| Atorvastatin (3 mg/kg/day) + dexamethasone (0.5 mg/kg/day) | 30 | 1 | 1 | 2 |
| Total number | 88 | 10 | 6 | 11 |

3. Pre-Clinical Experiments Showed that Use of the Atorvastatin Alone Promoted Absorption of Hematoma, but the Hematoma Absorption Speed was Low and Some Patients Were Not Sensitive to the Drug; and Use of a Small Dose of Dexamethasone Alone Exerted a Poor Hematoma Absorption Effect.

52 patients were orally and alone administered with the atorvastatin (in the first week, atorvastatin 10 mg, 3 times per day; in the second to third weeks, atorvastatin 10 mg, 2 times per day; in the fourth week, atorvastatin 10 mg, 1 time per day; and after the fourth week, atorvastatin 10 mg per day until the hematoma was absorbed or the hematoma was stable without any changes). Before treatment, the patients had a hematoma amount of 55.94±30.58 ml, and upon treatment for one month, conservatively successful patients had a hematoma amount of 28.29±29.47 ml. One month after administration of the drug, an average hematoma absorption rate was 49.43%, and an average administration period was 3.23 months. Among the 52 patients, 7 patients had a poor hematoma absorption effect after being administered with the atorvastatin, 3 patients were transferred to the group of the atorvastatin+a small dose of dexamethasone; and after treatment, the hematoma of the 3 patients was stable and was then gradually absorbed (see Table 2).

TABLE 2

Treatment of 52 patients with alone and orally administered atorvastatin

| Serial number | Age | Hematoma amount before entry into the group (ml) | Hematoma amount in the fourth week (ml) | Reduced hematoma amount in the fourth week (ml) |
|---|---|---|---|---|
| 1 | 79 | 80 | 40 | 40 |
| 2 | 60 | 27 | 6 | 21 |
| 3 | 75 | 60 | 15 | 45 |
| 4 | 83 | 67.5 | 30 | 37.5 |
| 5 | 75 | 50 | 20 | 30 |
| 6 | 67 | 40 | 0 | 40 |
| 7 | 70 | 30 | 20 | 10 |
| 8 | 25 | 15 | 0 | 15 |
| 9 | 81 | 70.4 | 30 | 40.4 |
| 10 | 46 | 57.5 | 0 | 57.5 |
| 11 | 68 | 60 | 30 | 30 |
| 12 | 79 | 45 | 0 | 45 |
| 13 | 81 | 49.5 | 27 | 22.5 |
| 14 | 66 | 23.75 | 17.5 | 6.25 |
| 15 | 69 | 59.85 | 20.5 | 39.35 |
| 16 | 63 | 35 | 0 | 35 |
| 17 | 68 | 48 | 0 | 48 |
| 18 | 74 | 16 | 4 | 12 |
| 19 | 59 | 72 | 48 | 24 |
| 20 | 37 | 29.7 | 10.6 | 19.1 |
| 21 | 80 | 46.2 | 23.4 | 22.8 |
| 22 | 79 | 89 | 24 | 65 |
| 23 | 79 | 89 | Surgical treatment | Surgical treatment |
| 24 | 70 | 107.90 | 146.85 | Surgical treatment |
| 25 | 68 | 177.45 | 138.60 | 38.85 |
| 26 | 58 | 52.5. | 15.00 | 37.5 |
| 27 | 74 | 66.0 | 29.25 | 36.75 |
| 28 | 66 | 73.13 | 81.90 | −8.775 |
| 29 | 68 | 47.25 | 38.00 | 9.25 |
| 30 | 83 | 123.75 | 30.00 | 93.75 |
| 31 | 70 | 83.16 | 36.00 | 47.16 |
| 32 | 79 | 131.04 | The effect was poor and hormone was used | The effect was poor and hormone was used |
| 33 | 66 | 73.13 | 35.00 | 38.125 |
| 34 | 58 | 55.00 | 40.00 | 15 |
| 35 | 56 | 45.00 | 30.00 | 15 |
| 36 | 50 | 33.00 | 25.00 | 8 |
| 37 | 59 | 42.35 | 26.00 | 16.35 |
| 38 | 66 | 55.00 | 40.00 | 15 |
| 39 | 62 | 40.00 | 38.00 | 2 |
| 40 | 64 | 65.00 | 45.00 | 20 |
| 41 | 68 | 35.00 | 30.00 | The effect was poor and hormone was used |
| 42 | 56 | 30.00 | 5.00 | 25 |
| 43 | 58 | 40.00 | 18.00 | 22 |
| 44 | 75 | 42.00 | 25.00 | 17 |
| 45 | 72 | 35.00 | 10.00 | 25 |
| 46 | 68 | 35.00 | 5.00 | 30 |
| 47 | 78 | 68.00 | Surgical treatment | Surgical treatment |
| 48 | 75 | 78.00 | Surgical treatment | Surgical treatment |
| 49 | 69 | 42.00 | 35.00 | 7 |
| 50 | 50 | 26.00 | 0.00 | 26 |
| 51 | 45 | 29.00 | 41.00 | −12 |
| 52 | 32 | 18.00 | The effect was poor and hormone was used | The effect was poor and hormone was used |
| Average value | 65.9 | 55.94 ml | 28.29 ml | 49% (hematoma absorption rate) |

15 patients were orally and alone administered with a small dose of dexamethasone (in the first week, dexamethasone 0.75 mg, 3 times per day; in the second to third weeks, dexamethasone 0.75 mg, 2 times per day; in the fourth week, dexamethasone 0.75 mg, 1 time per day; after the fourth week, 0.75 mg of dexamethasone per day until the hematoma was absorbed or the hematoma was stable without any changes). Before treatment, the patients had a hematoma amount of 79.97±21.00 ml ml, and upon treatment for one month, conservatively successful patients had a hematoma amount of 50.86±24.52 ml. One month after administration of the drug, an average hematoma absorption rate was 24.71%. Among the 15 patients, no therapeutic effect was exerted for 5 patients after the patients were singly administered with dexamethasone, and these 5 patients were transferred to surgical treatment for removing the hematoma (see Table 3).

TABLE 3

Treatment of 15 patients with a small dose of dexamethasone

| Serial number | Age | Hematoma amount before entry into the group (ml) | Hematoma amount in the fourth week (ml) | Reduced hematoma amount in the fourth week (ml) | Hematoma absorption rate in the fourth week (%) |
|---|---|---|---|---|---|
| 1 | 66 | 75.04 | Surgical treatment | Surgical treatment | Surgical treatment |
| 2 | 58 | 61.88 | 40.95 | 20.93 | 0.34 |
| 3 | 56 | 105.00 | 80.00 | 25.00 | 0.24 |
| 4 | 50 | 82.23 | Surgical treatment | Surgical treatment | Surgical treatment |
| 5 | 59 | 75.94 | 36.30 | 39.64 | 0.52 |
| 6 | 66 | 56.62 | 32.73 | 23.90 | 0.42 |
| 7 | 62 | 62.40 | Surgical | Surgical | Surgical |

TABLE 3-continued

Treatment of 15 patients with a small dose of dexamethasone

| Serial number | Age | Hematoma amount before entry into the group (ml) | Hematoma amount in the fourth week (ml) | Reduced hematoma amount in the fourth week (ml) | Hematoma absorption rate in the fourth week (%) |
|---|---|---|---|---|---|
| 8 | 64 | 104.65 | 96.53 | 8.13 | 0.08 |
| 9 | 68 | 78.30 | 39.88 | 38.43 | 0.49 |
| 10 | 56 | 54.33 | 30.25 | 24.08 | 0.44 |
| 11 | 58 | 117.00 | Surgical treatment | Surgical treatment | Surgical treatment |
| 12 | 75 | 71.40 | 35.00 | 36.40 | 0.51 |
| 13 | 72 | 107.25 | Surgical treatment | Surgical treatment | Surgical treatment |
| 14 | 68 | 93.60 | 80.00 | 13.60 | 0.15 |
| 15 | 78 | 54.00 | 37.00 | 17.00 | 0.31 |
| Average value | | 79.97 ml | 50.86 ml | 24.71 ml | 35% |

The experiment results showed that use of statin alone achieved the effects of regulating local capsular vessel formation, promoting mature of capsular neovascularization, stabilizing vascular intima, inhibiting local exception inflammatory reactions, and reducing vascular exudation. However, the effect of inhibiting local exception inflammatory reactions is weak, and use of glucocorticoids alone still fails to achieve the effects of vascularization and intima stabilization. The combination of the two drugs achieves a synergistic effect, remarkably shortens the onset time of the drugs, accelerates absorption of hematoma, and reduces the adverse complications caused by the hormone.

4. Specific Schemes of Treatment for Chronic Subdural Hematoma Using the Statin in Combination with a Small Dose of Dexamethasone In addition to receiving the conventional treatment, a specific method of taking the pharmaceutical composition according to the present invention was as follows (the clinical test results were as listed in Table 4):
in the first week: atorvastatin 10 mg+dexamethasone 0.75 mg, 3 times per day;
in the second to third weeks: atorvastatin 10 mg+dexamethasone 0.75 mg, 2 times per day; and
in the fourth week: atorvastatin 10 mg+dexamethasone 0.75 mg, 1 time per day.

TABLE 4

Treatment of 11 patients with a combination of statin and a small dose of dexamethasone

| Serial number | Age | Hematoma amount before entry into the group (ml) | Hematoma amount in the second week (ml) | Hematoma absorption rate in the second week (%) | Hematoma amount in the fourth week (ml) | Hematoma absorption rate in the fourth week (%) | Hematoma amount in the third month (ml) | Hematoma absorption rate in the third month (%) |
|---|---|---|---|---|---|---|---|---|
| 1 | 20 | 61.88 | 40.95 | 0.34 | 34.65 | 0.44 | 12.00 | 0.81 |
| 2 | 90 | 105.00 | 40.00 | 0.62 | 0 | 1.00 | 0 | 1.00 |
| 3 | 72 | 83.23 | 20.00 | 0.76 | 0 | 1.00 | 0 | 1.00 |
| 4 | 77 | 75.94 | 36.30 | 0.52 | 16.20 | 0.79 | 0 | 1.00 |
| 5 | 75 | 56.62 | 32.73 | 0.42 | 16.80 | 0.70 | 0 | 1.00 |
| 6 | 56 | 104.65 | 96.53 | 0.08 | 77.19 | 0.26 | 20.00 | 0.81 |
| 7 | 82 | 78.30 | 39.88 | 0.49 | 0 | 1.00 | 0 | 1.00 |
| 8 | 61 | 54.33 | 30.25 | 0.44 | 28.79 | 0.47 | 18.65 | 0.66 |
| 9 | 66 | 117.00 | 80.00 | 0.32 | 18.00 | 0.85 | 0 | 1.00 |
| 10 | 82 | 71.40 | 35.00 | 0.51 | 10.00 | 0.86 | 0 | 1.00 |
| 11 | 78 | 54.00 | 37.00 | 0.31 | 25.00 | 0.54 | 8.00 | 0.85 |
| Average value | 69 | 78.30 | 44.42 | 44% | 20.60 | 72% | 5.33 | 95% |

The clinical experiments showed that after the 11 patients were subjected to a joint treatment with statin and a small dose of dexamethasone, the hematoma was quickly absorbed, and no obvious complications and no drug adverse effects occurred.

5. Typical Case Exhibition

Figure 11:
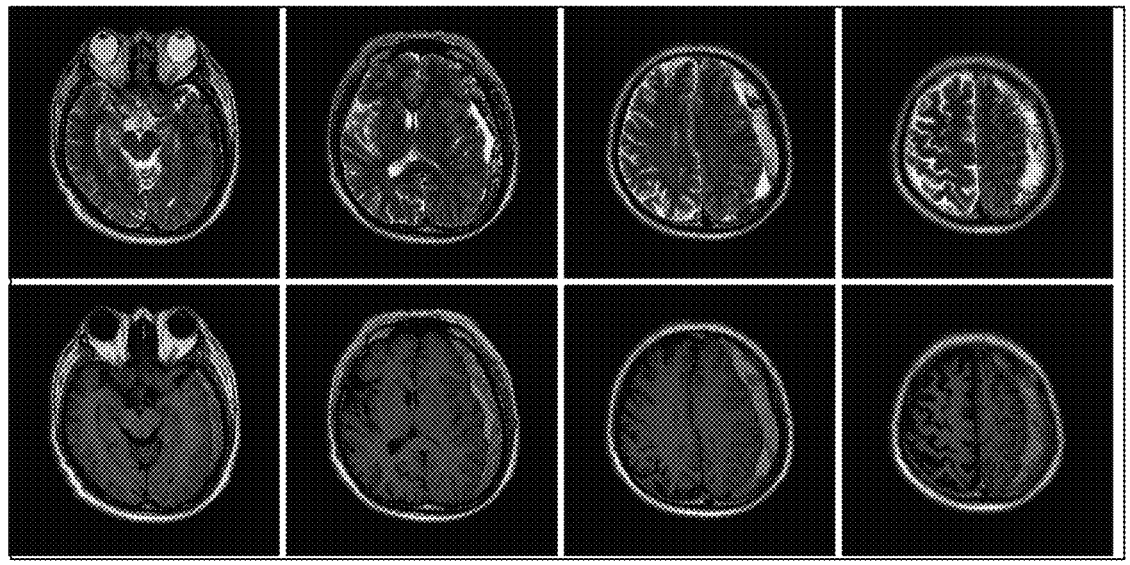
FIG. 11 is a head CT diagram of a patient before treatment.

In Table 1, No. 9 patient's head was injured about one month ago, and the examination carried out two days after limbs' activities were limited found subdural hematoma with a hematoma amount of about 117 ml, the midline shifted towards the right significantly (see FIG. 11), and through a joint treatment with atorvastatin and a small dose of dexamethasone, the hematoma was gradually absorbed, and the surgical treatment was avoided.

Figure 12:
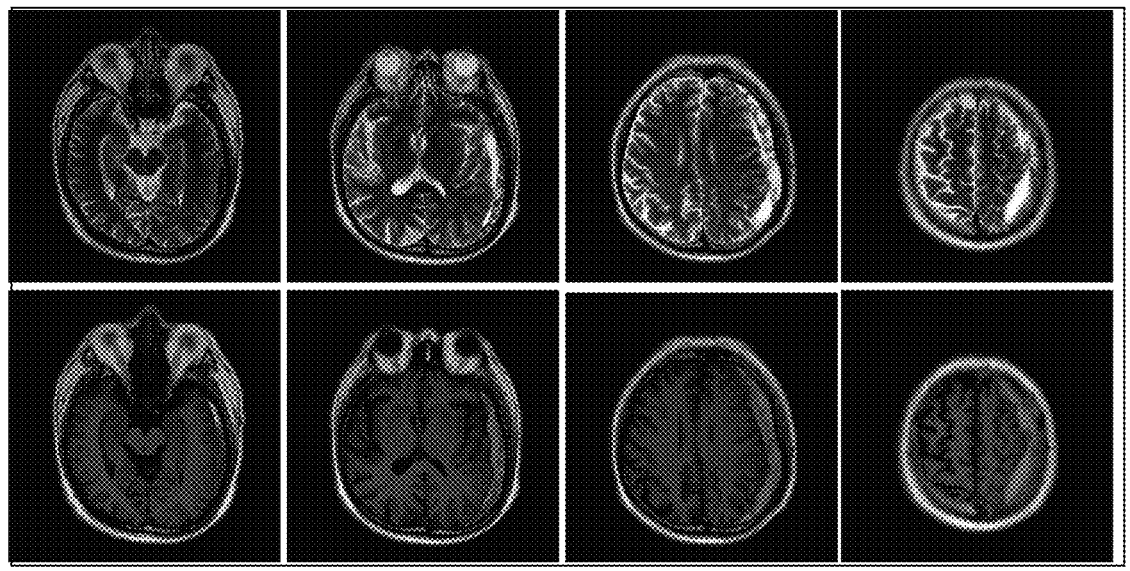
FIG. 12 is a head CT diagram of a patient after treatment using a pharmaceutical composition for 2 weeks according to the present invention.

FIG. 12 shows that the hematoma of the patient is obviously absorbed two weeks upon the treatment, the midline shift is improved, and the hematoma amount is 80 ml.

Figure 13:
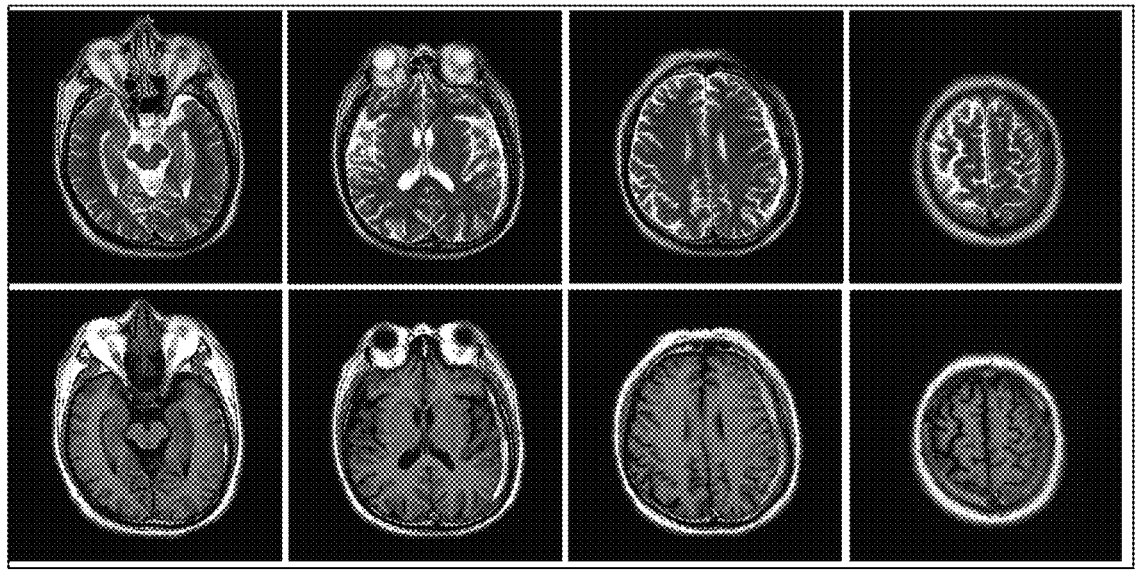
FIG. 13 is a head CT diagram of a patient after treatment using a pharmaceutical composition for four weeks according to the present invention.

FIG. 13 shows that the hematoma of the patient is mostly and significantly absorbed four weeks upon the treatment, the midline shift is eliminated, and the hematoma amount is 18 ml.

Figure 14:
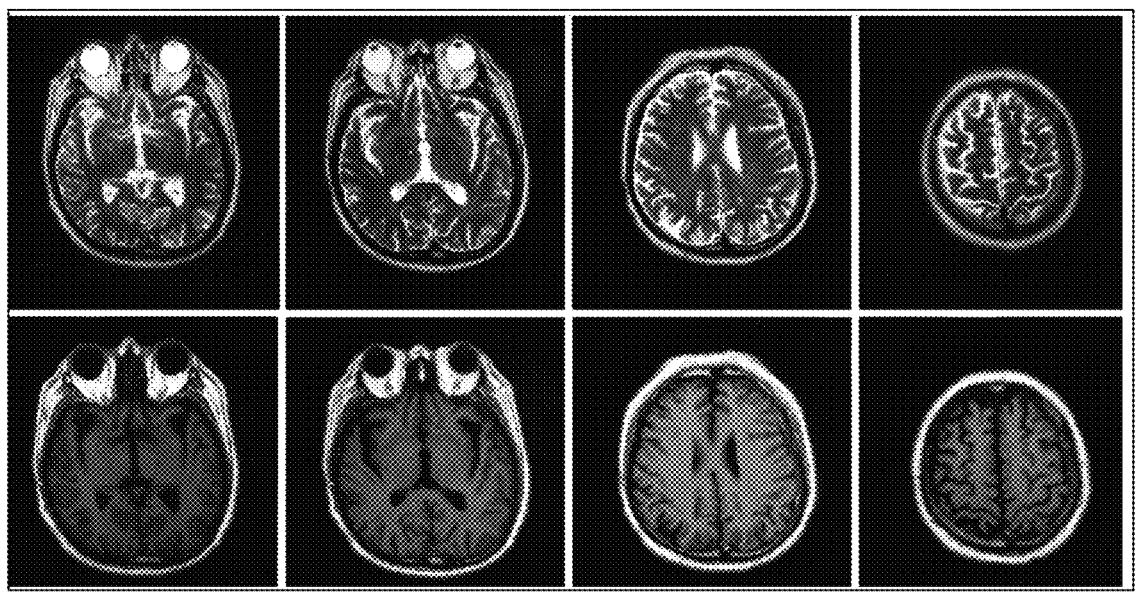
FIG. 14 is a head CT diagram of a patient who is administered with atorvastatin for three months after treatment using a pharmaceutical composition for four weeks according to the present invention.

FIG. 14 shows that the hematoma of the patient absolutely disappears after the patient continues to be administered with atorvastatin for three months upon four-week treatment.

Figure 15:
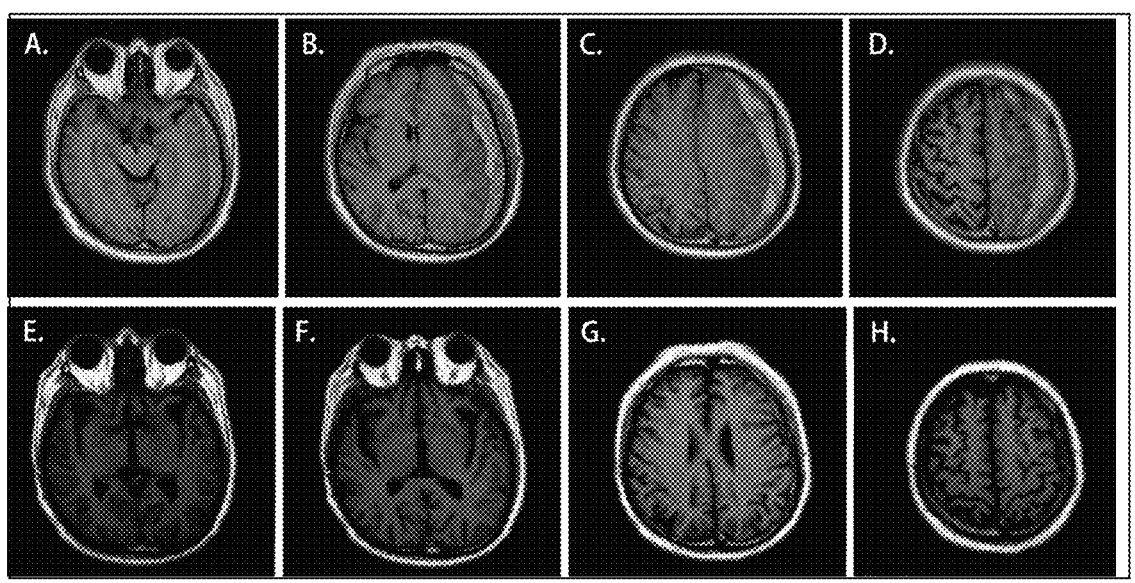
FIG. 15 is a comparison of head CT diagrams of a patient before and after treatment.

FIG. 15 is a comparison of head CT diagrams of a patient before and after treatment, wherein A-D show that the amount of the chronic subdural hematoma before treatment is large, the midline shift is obvious; and E-H show that hematoma of the patient absolutely disappears after the patient continues to be administered with atorvastatin for three months upon four-week treatment.

6. Effect Mechanism of Treatment for Chronic Subdural Hematoma Using the Statin in Combination with a Small Dose of Dexamethasone Hydroxymethylglutaryl coenzyme A reductase inhibitor-statin is currently widely confirmed as an effective drug that can promote angiogenesis after nerve injury, in addition to lipid-lowering. It has been reported that statin can promote the mobilization of circulating blood endothelial progenitor cells, and maintain endothelial progenitor cells at a higher level for more than 14 days. At the same time, atorvastatin has been shown to significantly inhibit VEGF, and can significantly reduce inflammation-related factors and inflammatory response. It has been further reported that statin can also promote sustained expression of Notch1/Jagged1 signals, both of which are critical signals for the regulation maturity of angiogenesis by VEGF. Recent animal experiments have found that a small dose of atorvastatin can affect low expressions of vascular endothelial cell factors VEFG, TGF-β, MMP-9, stabilize the Ang-1/Ang-2 ratio, and can significantly reduce local TNF-α and IL-6 gene and protein levels in the hematoma capsule. The above results show that statin promotes the subdural hematoma absorption mechanism, regulate local capsular vessel formation, promoting mature of capsular neovascularization, stabilize vascular intima, inhibiting local exception inflammatory reactions, and reduce vascular exudation.

Dexamethasone inhibits the formation of a new hematoma capsule in a rat model of subdural hematoma. Combined with the strong inflammarion inhibition effect of glucocorticoid, the effects of the statin in inhibiting local abnormal inflammatory response and reducing vascular exudation may be significantly enhanced. Based on the existing experimental theory, the mechanism of glucocorticoid in the treatment of chronic subdural hematoma is that glucocorticoid reduces the inflammatory reaction, thereby hindering inflammatory cytokine-mediated abnormal angiogenesis, reducing plasma plasminogen and VEGF, and reducing vascular permeability. In addition, because of the strong local inflammation inhibitory effect, the glucocorticoid having a synergistic effect with statin achieves the effect of promoting rapid absorption of hematoma which is also achieved by a small dose of dexamethasone.

What is claimed is:

1. A method for treatment of chronic subdural hematoma, comprising administering an effective amount of a drug to a subject of the treatment, wherein said drug comprises a statin and an adrenocortical hormone, wherein the statin is atorvastatin and the adrenocortical hormone is dexamethasone;

wherein the administration regimen of the atorvastatin and the dexamethasone is as follows:
in the first week: atorvastatin 10 m+dexamethasone 0.75 mg, 3 times per day;
in the second to third weeks: atorvastatin 10 and dexamethasone 0.75 mg, 2 times per day; and
in the fourth week: atorvastatin 10 mg+dexamethasone 0.75 mg, 1 time per day.

2. The method according to claim 1, wherein a mass ratio of the atorvastatin to the dexamethasone is 40:3.

* * * * *